United States Patent
Yasuda et al.

(10) Patent No.: US 7,053,050 B2
(45) Date of Patent: May 30, 2006

(54) PREVENTIVES/REMEDIES FOR PROLIFERATIVE ORGAN DISEASES CHRONIC ARTHRITIC DISEASES, HYPERTROPHIC SCAR OR KELOID

(75) Inventors: Yoshiko Yasuda, Kyoto (JP); Yukio Nakamura, Higashimurayama (JP); Yoshihiko Fujita, Sakai (JP)

(73) Assignee: Yoshiko Yasuda, Kyoto (JP)

( * ) Notice: Subject to any disclaimer, the term of this patent is extended or adjusted under 35 U.S.C. 154(b) by 25 days.

(21) Appl. No.: 10/494,433

(22) PCT Filed: Nov. 1, 2002

(86) PCT No.: PCT/JP02/11442

§ 371 (c)(1),
(2), (4) Date: Apr. 30, 2004

(87) PCT Pub. No.: WO03/037377

PCT Pub. Date: May 8, 2003

(65) Prior Publication Data

US 2004/0266676 A1    Dec. 30, 2004

(30) Foreign Application Priority Data

Nov. 2, 2001    (JP) ............................. 2001-337588

(51) Int. Cl.
*A61K 38/00*    (2006.01)
(52) U.S. Cl. ...................................... 514/12
(58) Field of Classification Search ............... 530/350; 514/2, 12
See application file for complete search history.

(56) References Cited

U.S. PATENT DOCUMENTS

| 5,767,078 A | * | 6/1998 | Johnson et al. ............... 514/12 |
| 5,773,569 A | * | 6/1998 | Wrighton et al. ........... 530/300 |
| 5,885,574 A | * | 3/1999 | Elliott ..................... 424/133.1 |

FOREIGN PATENT DOCUMENTS

| JP | 10-101574 | 4/1998 | |
| WO | 96/08240 | 3/1996 | |
| WO | 96/20728 | 7/1996 | |
| WO | 97/18805 | 5/1997 | |
| WO | WO 98/10650 | * 3/1998 | .................. 514/12 |
| WO | 99/15648 | 4/1999 | |
| WO | 00/66632 | 11/2000 | |
| WO | 02/43572 | 6/2002 | |

OTHER PUBLICATIONS

Johnson et al. "Identification of a 13 Amino Acid Peptide Mimetic of Erythropoietin and Description of Amino Acids Critical for the Mimetic Activity of EMP1," Biochemistry (1998), V. 37, pp. 3699-3710.*

* cited by examiner

*Primary Examiner*—Karen Cochrane Carlson
*Assistant Examiner*—Agnes Rooke
(74) *Attorney, Agent, or Firm*—Wenderoth, Lind & Ponack L.L.P.

(57) ABSTRACT

An agent for prophylaxis or treatment of proliferative organ diseases, chronic arthritic diseases, hypertrophic scars or keloid, comprising an erythropoietin receptor antagonist or a salt thereof.

11 Claims, No Drawings

SEQUENCE LISTING

```
<160> NUMBER OF SEQ ID NOS: 1

<210> SEQ ID NO 1
<211> LENGTH: 20
<212> TYPE: PRT
<213> ORGANISM: Human
<300> PUBLICATION INFORMATION:
<301> AUTHORS: Dana L. Johnson et al
<302> TITLE: Identification of a 13 Amino Acid Peptide Mimetic of
       Erythropoietin and Description of Amino Acids Critical for the
       Mimetic Activity of EMP1
<303> JOURNAL: Biochemistry
<304> VOLUME: 37
<305> ISSUE: 11
<306> PAGES: 3699-3710

<400> SEQUENCE: 1

Gly Gly Thr Tyr Ser Cys His Phe Ala Pro Leu Thr Trp Val Cys
1               5                   10                  15

Lys Pro Gln Gly Gly
                20
```

PREVENTIVES/REMEDIES FOR PROLIFERATIVE ORGAN DISEASES CHRONIC ARTHRITIC DISEASES, HYPERTROPHIC SCAR OR KELOID

This application is a U.S. national stage of International Application No. PCT/JP02/11442 filed Nov. 1, 2002.

TECHNICAL FIELD

The present invention relates to an agent for prophylaxis or treatment of proliferative organ diseases, chronic arthritic diseases, and hypertrophic scars or keloid, comprising an erythropoietin receptor antagonist, etc.

BACKGROUND ART

As a therapeutic method for proliferative organ diseases such as cancer and proliferative lesion in tissues or organs, surgical dissection, irradiation, administration of anticancer agents or combination thereof has been conventionally used. However, basic and specific investigations for the biological characteristics of cancer itself fall behind the remarkable progress of diagnosis technologies for cancer. Therefore, under the present circumstances, drastic therapy of cancer has not been established yet.

Erythropoietin is involved in proliferation and differentiation of hematocytes. Unlike other cytokines, erythropoietin is not produced in hematocyte but produced in kidneys or liver and released into blood. Erythropoietin is considered to act on erythroid burst forming cell (BFU-E) and erythroid colony forming cell (CFU-E) among erythroid precursor cells, stimulate their proliferation and differentiation, and induce production of erythrocytes (Krantz S. B., Blood, Vol. 77, pp. 419–434 (1991)). It has been considered that when erythropoietin binds to a erythropoietin receptor existing on the cell membrane of a precursor cell, a signal is transmitted into the cell nucleus to cause differentiation into an erythrocyte, i.e., accumulation of globin mRNA in the cell, production of hemoglobin and differentiation into an erythrocyte (D' Andrea A. D. et al., Cell, Vol. 57, pp. 277–285 (1989)). However, the detailed mechanism thereof has not yet been clarified, and many problems still remain to be solved.

As the sites on which erythropoietin expresses its gene among tissues except the sites relating to erythroblast, embryos of the early post-implantation stage (Yasuda Y. et al., Develop. Growth Differ., Vol. 35, pp. 711–722 (1993)), brains of humans, monkeys and mice (Marti H. H. et al., Eur. J. Neu. Sci., Vol. 8, pp. 666–676 (1996)) and endometria of mice (Yasuda Y. et al., J. Biol. Chem., Vol. 273, pp. 25381–25387 (1998)) are known. Furthermore, the present inventors have been found that the erythropoietin receptor gene is expressed on mouse deciduae (Yasuda Y. et al., Develop. Growth Differ., Vol. 35, pp. 711–722 (1993)) and vascular endothelium cells of mouse endometrium (Yasuda Y. et al., J. Biol. Chem., Vol. 273, pp. 25381–25387 (1998)) in addition to erythroblasts. Under the present circumstance, the functions of erythropoietin or erythropoietin receptor genes on such sites other than hematocytes have not been revealed yet.

When an embryo nidates on an endometrium, the implantation site of the endometrium undergoes decidual reaction, whereby the deciduae surround the embryo. The erythropoietin receptor gene is expressed on deciduae, whereas erythropoietin is not expressed thereon. Accordingly, it is considered that the erythropoietin receptor is produced on deciduae and bound to the erythropoietin in blood to transmit the erythropoietin signal. According to the investigation on normal human endometrium, expression of the erythropoietin gene could be observed in some samples and could not be observed in other samples by the present technology. However, expressions of erythropoietin and an erythropoietin receptor at the level of protein were observed in all samples. Accordingly, it is considered that erythropoietin is taken from blood or self-secreted at the extremely low concentration in the human normal endometrium, which is similar to the case of the deciduae, and involved in normal physiological function of uterus. On the other hand, it has been recognized by RT-PCR and Southern Blot method that the erythropoietin mRNA is expressed on cervical cancer, corpus uteri cancer, hysteromyoma, ovarian cancer, and ovarian cystoma. Furthermore, an erythropoietin receptor is expressed on the vascular endothelium cells in these cancer tissues. The investigation on these tissues has revealed that erythropoietin and erythropoietin receptor proteins, as well as proliferative nuclear antigens exist on these cancer cells. Accordingly, it was presumed that erythropoietin is involved in proliferation of cancer cells.

Furthermore, it is disclosed that a substance that binds to an erythropoietin receptor in a specific domain can be used for therapy of chronic rheumatoid arthritis (WO00/66632).

Along the way, the present inventors have found that erythropoietin antagonists (the "erythropoietin antagonist" means a substance capable of binding to erythropoietin) such as erythropoietin antibodies, erythropoietin receptor proteins, etc., have an inhibitory effect on proliferation of cancer cells and an interrupting effect on intervening blood capillaries (JP-A-10-101574, British Journal of Cancer, Vol. 84, pp. 836–843 (2001)).

OBJECT OF THE INVENTION

However, all of these erythropoietin antagonists are proteins, and any low molecular weight compounds such as peptides having both an inhibitory effect on proliferation of cancer cells and an effect on vascular proliferation in cancer tissues by the similar action mechanism (blocking of the erythropoietin signal) have not been known yet. The present invention aims at providing a superior agent for prophylaxis or treatment of proliferative organ diseases, chronic arthritic diseases, and hypertrophic scars or keloid, etc., which comprises a low molecular weight compound such as peptide as an active component.

SUMMARY OF THE INVENTION

The present inventors have done intensive investigations to solve the above-mentioned problem, and found that a low molecular weight compound such as a peptide having erythropoietin receptor antagonism has unexpectedly superior inhibitory effects on proliferation of both a cancer cell and an intercalated blood vessel. Based on these findings, the present inventors have done further investigations, which resulted in completion of the present invention.

Namely, the present invention relates to:

[1] an agent for prophylaxis or treatment of proliferative organ diseases, chronic arthritic diseases, hypertrophic scars or keloid, comprising an erythropoietin receptor antagonist or a salt thereof;

[2] the agent according to the above-mentioned [1], wherein the erythropoietin receptor antagonist or a salt thereof is a low molecular weight erythropoietin receptor antagonist or a salt thereof;

[3] the agent according to the above-mentioned [1], wherein the erythropoietin receptor antagonist or a salt thereof is a low molecular weight peptidic erythropoietin receptor antagonist or a salt thereof;

[4] the agent according to the above-mentioned [1], wherein the erythropoietin receptor antagonist or a salt thereof is an erythropoietin mimetic peptide or a salt thereof;

[5] the agent according to the above-mentioned [1], wherein the erythropoietin receptor antagonist or a salt thereof is erythropoietin mimetic peptide 9 or a salt thereof;

[6] the agent according to the above-mentioned [1], wherein the erythropoietin receptor antagonist or a salt thereof is a peptide comprising an amino acid sequence identical or substantially identical with the amino acid sequence of SEQ ID NO: 1 or a salt thereof;

[7] the agent according to the above-mentioned [1], wherein the erythropoietin receptor antagonist or a salt thereof is an anti-erythropoietin receptor antibody or a salt thereof;

[8] the agent according to the above-mentioned [1], wherein the proliferative organ disease is cancer or tumor;

[9] the agent according to the above-mentioned [1], wherein the chronic arthritic disease is rheumatoid arthritis, rheumatoid diseases, chronic arthritis of collagenosis or tendovaginitis;

[10] a vascular proliferation suppressing agent comprising an erythropoietin receptor antagonist or a salt thereof;

[11] a method for prophylaxis or treatment of proliferative organ diseases, chronic arthritic diseases, hypertrophic scars or keloid, comprising administering an effective amount of an erythropoietin receptor antagonist or a salt thereof to a mammal;

[12] a method for prophylaxis or treatment of proliferative organ diseases, comprising administering an effective amount of an erythropoietin receptor antagonist or a salt thereof in combination with an effective amount of another anticancer agent or a salt thereof to a mammal;

[13] use of an erythropoietin receptor antagonist or a salt thereof for production of an agent for prophylaxis or treatment of proliferative organ diseases, chronic arthritic diseases, hypertrophic scars or keloid, etc.

DETAILED DESCRIPTION OF THE INVENTION

The erythropoietin receptor antagonist used for the agent for prophylaxis or treatment of proliferative organ diseases, chronic arthritic diseases, hypertrophic scars or keloid of the present invention (hereinafter abbreviated to as "the agent of the present invention") is not specifically limited as long as it is a substance that blocks the signaling from an erythropoietin receptor by competitively or non-competitively inhibiting binding of erythropoietin to the human erythropoietin receptor, or a substance that blocks the signaling from an erythropoietin receptor without inhibiting binding of erythropoietin to the human erythropoietin receptor (e.g., a substance that inhibits JAK2 kinase, etc.). For example, anti-erythropoietin receptor antibodies, etc. are included.

Among these, preferred erythropoietin receptor antagonist is a low molecular weight compound having a molecular weight of about 200 to 5000 and specifically a low molecular weight compound having a molecular weight of about 300 to 3000. Although the erythropoietin receptor antagonist may be peptidic or non-peptidic, it is preferably peptidic and more preferably peptidic one having a low molecular weight.

The low molecular peptide used for the present invention includes, for example, a peptide consisting of at least 5 or more, preferably about 5 to 30, specifically preferably about 15 to 25 of amino acid residues, etc.

The erythropoietin mimetic peptide (EMP) used for the present invention is not specifically limited as long as it is a peptide that blocks the signaling from an erythropoietin receptor by binding to the human erythropoietin receptor with the strength of binding between a ligand and a receptor, or a peptide that blocks the signaling from an erythropoietin receptor without binding to the human erythropoietin receptor (e.g., a peptide that inhibits JAK2 kinase, etc.). For example, erythropoietin mimetic peptides (EMPs) described in Biochemistry 37, 3699, 1998 are included. Among these, EMP6, EMP7, EMP9, EMP12, EMP22, EMP23, EMP24, EMP25, EMP33 and EMP39 are preferred, and EMP9 is specifically preferred.

More specifically, for example, a peptide comprising an amino acid sequence identical or substantially identical with the amino acid sequence represented by SEQ ID NO: 1, etc. is used as the erythropoietin receptor antagonist. The peptide may be any of peptides, synthetic peptides and recombinant peptides derived from any cells of mammals (e.g., guinea pig, rat, mouse, chicken, rabbit, swine, sheep, bovine, monkey, human, etc.), for example, hepatic cells, spleen cells, nerve cells, glia cells, β-cells of pancreas, bone marrow cells, mesangial cells, Langerhans' cells, epidermal cells, epithelial cells, endothelial cells, fibroblasts, fibrocytes, striated muscle cells, smooth muscle cells, fat cells, immunocytes (e.g., macrophage, T cells, B cells, natural killer cells, mast cells, neutrophils, basophils, eosinophils, monocytes, etc.), megakaryocytes, synovial cells, chondrocytes, osteocytes, osteoblasts, osteoclasts, mammary gland cells or interstitial cells, or precursor cells, stem cells or cancerous cells thereof, etc., or any tissues containing such cells, for example, brain, various parts of brain (e.g., olfactory bulb, amygdala, cerebral basal ganglia, hippocampus, thalamus, hypothalamus, diencephalic cerebral cortex, medulla oblongata, cerebellum), spinal cord, pituitary, stomach, pancreas, kidney, liver, genital gland, thyroid gland, gallbladder, bone marrow, adrenal gland, skin, muscle, lung, digestive tract (e.g., large intestine, small intestine), blood vessel, heart, thymus, spleen, sublingual gland, parotid gland, peripheral blood, prostate, testis, ovary, placenta, uterus, bone, joint, skeletal muscle and connective tissues of these tissues, etc., or hematocyte cells or cultured cell strains thereof, etc.

The peptide comprising an amino acid sequence substantially identical with the amino acid sequence represented by SEQ ID NO: 1 includes a peptide comprising an amino acid sequence having at least about 70% homology, preferably at least about 80% homology, more preferably at least about 90% homology, most preferably at least about 95% homology, to the amino acid sequence represented by SEQ ID NO: 1, etc.

Furthermore, as the erythropoietin receptor antagonist, for example, a peptide comprising an amino acid sequence in which 1 or 2 or more (preferably about 1 to 7, more preferably about 1 to 5, more preferably 1 to 3) of amino acids have been deleted from the amino acid sequence represented by SEQ ID NO: 1; a peptide comprising an amino acid sequence in which 1 or 2 or more (preferably about 1 to 7, more preferably about 1 to 5, more preferably 1 to 3) of amino acids have been added to or inserted in the amino acid sequence represented by SEQ ID NO: 1; a peptide comprising an amino acid sequence in which 1 or 2 or more (preferably about 1 to 7, more preferably about 1 to 5, more preferably 1 to 3) of amino acids have been replaced with other amino acids in the amino acid sequence represented by SEQ ID NO: 1; or a peptide comprising a combination of the above-mentioned amino acid sequences, etc. can be used.

The other amino acids as used herein may be either natural type or non-natural type.

The erythropoietin receptor antagonist is designated by the conventional way of describing peptides. That is, the left end is the N-terminal (amino terminal) and the right end is the C-terminal (carboxyl terminal). In the erythropoietin receptor antagonist including a low molecular peptide having the amino acid sequence represented by SEQ ID No: 1, the C-terminal is normally a carboxyl group (—COOH) or carboxylate (—COO$^-$), but the C-terminal may be an amide (—CONH$_2$) or an ester (—COOR).

Examples of the ester group shown by R include a $C_{1-6}$ alkyl group such as methyl, ethyl, n-propyl, isopropyl or n-butyl; a $C_{3-8}$ cycloalkyl group such as cyclopentyl or cyclohexyl; a $C_{6-12}$ aryl group such as phenyl or α-naphthyl; a $C_{6-12}$ aryl–$C_{1-2}$ alkyl group such as benzyl, phenethyl or α-naphthylmethyl, etc. In addition, pivaloyloxymethyl ester, etc. that is used generally as an ester for oral administration may also be used.

In the case wherein the erythropoietin receptor antagonist contains a carboxyl group (or carboxylate) at a position other than the C-terminal, the carboxyl group may be amidated or esterified, and such amide or ester is also included within the low molecular peptide of the present invention. In this case, the ester group may be the same group as that described with respect to the above C-terminal.

Furthermore, the erythropoietin receptor antagonist includes derivatives wherein a group (e.g., OH, COOH, NH$_2$, SH, etc.) on the side chains of an amino acid in the molecule is protected with a suitable protecting group (e.g., a $C_{1-6}$ acyl group such as a formyl group, an acetyl group, etc.), or conjugated peptides such as glycopeptides with sugar chains attached thereto.

As a specific example of the erythropoietin receptor antagonist, erythropoietin mimetic peptide 9 (EMP9) consisting of the amino acid sequence represented by SEQ ID NO: 1 is preferably used.

A salt of the erythropoietin receptor antagonist is preferably in the form of physiologically acceptable acid addition salts. Examples of such salts include salts with inorganic acids (e.g., hydrochloric acid, phosphoric acid, hydrobromic acid, sulfuric acid), salts with organic acids (e.g., acetic acid, formic acid, propionic acid, fumaric acid, maleic acid, succinic acid, tartaric acid, citric acid, malic acid, oxalic acid, benzoic acid, methanesulfonic acid, benzenesulfonic acid, aspartic acid, glutamic acid, etc.), etc. Salts with inorganic bases (e.g., alkali metal such as sodium, potassium, etc., alkaline earth metal such as calcium, magnesium, etc., aluminum or ammonium, etc.), salts with organic bases (e.g., trimethylamine, triethylamine, pyridine, picoline, 2,6-lutidine, ethanolamine, diethanolamine, triethanolamine, cyclohexylamine, dicyclohexylamine, N,N'-dibenzylethylenediamine, lysine, arginine, histidine, etc.), etc. can be also used.

A prodrug of the erythropoietin receptor antagonist or a salt thereof to be contained in the agent of the present invention refers to a compound that converts to an erythropoietin receptor antagonist by reaction of an enzyme, gastric acid, etc. under physiological conditions in vivo, i.e., a compound that undergoes enzymatic oxidation, reduction or hydrolysis, etc. and thereby converts to an erythropoietin receptor antagonist, or a compound that undergoes hydrolysis, etc. by gastric acid, etc. and thereby converts to an erythropoietin receptor antagonist.

Examples of the prodrugs of the erythropoietin receptor antagonist or a salt thereof to be contained in the agent of the present invention include compounds derived by acylation, alkylation or phosphorylation of the amino group of the low molecular peptide to be contained in the agent of the present invention (e.g., compounds derived by eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation or tert-butylation of the amino group of the low molecular peptide to be contained in the agent of the present invention); compounds derived by acylation, alkylation, phosphorylation or boration of the hydroxyl group of the low molecular peptide to be contained in the agent of the present invention (e.g., compounds derived by acetylation, palmitoylation, propanoylation, pivaloylation, succinylation, fumarylation, alanylation or dimethylaminomethylcarbonylation of the hydroxyl group of the low molecular peptide to be contained in the agent of the present invention); and compounds derived by esterification or amidation of the carboxyl group of the low molecular peptide to be contained in the agent of the present invention (e.g., compounds derived by ethyl esterification, phenyl esterification, carboxymethyl esterification, dimethylaminomethyl esterification, pivaloyloxymethyl esterification, ethoxycarbonyloxyethyl esterification, phthalidyl esterification, (5-methyl-2-oxo-1,3-dioxolen-4-yl)methyl esterification, cyclohexyloxycarbonylethyl esterification, or methylamidation of the carboxyl group of the low molecular peptide to be contained in the agent of the present invention), etc. These compounds can be produced from the low molecular peptide to be contained in the agent of the present invention by per se known methods.

The prodrug of the erythropoietin receptor antagonist or a salt thereof to be contained in the agent of the present invention may be a compound that converts to an erythropoietin receptor antagonist under physiological conditions as described in "Iyakuhin No Kaihatsu (Development of Drugs)", Vol. 7, Molecular Designing, published by Hirokawa Shoten, 1990, pages 163–198.

The erythropoietin receptor antagonist or a salt thereof to be contained in the agent of the present invention can be prepared by (1) a method known per se from the above-mentioned cells or tissues of mammals, (2) a peptide synthesis method, or (3) a method comprising culturing a transformant comprising DNA encoding a low molecular peptide to be contained in the agent of the present invention.

[Preparation Method from Mammalian Cells or Tissues]

When the erythropoietin receptor antagonist or a salt thereof is manufactured from human or mammalian tissues or cells, the human or mammalian tissues or cells are homogenized, and then extracted with an acid, etc. The extract can be isolated and purified by a combination of chromatography techniques such as reverse phase chromatography, ion exchange chromatography, etc.

[Preparation Method According to a Peptide Synthesis Method]

The erythropoietin receptor antagonist or a salt or an amide thereof to be contained in the agent of the present invention can be manufactured by a method for peptide synthesis known per se, or by cleaving erythropoietin with a suitable peptidase.

The peptide synthesis method may be, for example, a solid phase synthesis method or a liquid phase synthesis method. That is, a partial peptide or amino acids that can constitute the low molecular peptide to be contained in the agent of the present invention is condensed with the remaining part of the low molecular peptide and, if the product has a protecting group, it is removed to obtain the desired peptide. Examples of known methods for condensation and elimination of a protecting group are described in the following 1)–5).
1) M. Bodanszky & M. A. Ondetti: Peptide Synthesis, Interscience Publishers, New York (1966)
2) Schroeder & Luebke: The Peptide, Academic Press, New York (1965)
3) Nobuo Izumiya, et al.: Peptide Gosei-no-Kiso to Jikken (Basics and experiments of peptide synthesis), published by Maruzen Co. (1975)
4) Haruaki Yajima & Shunpei Sakakibara: Seikagaku Jikken Koza (Biochemical Experiment) 1, Tanpakushitsu no Kagaku (Chemistry of Proteins) IV, 205 (1977)
5) Haruaki Yajima ed.: Zoku Iyakuhin no Kaihatsu (A sequel to Development of Pharmaceuticals), Vol. 14, Peptide Synthesis, published by Hirokawa Shoten More specifically, in order to synthesize the erythropoietin receptor antagonist or a salt or an amide form thereof to be contained in the agent of the present invention, commercially available resins for peptide synthesis can be used. Examples of such resins include chloromethyl resin, hydroxymethyl resin, benzhydrylamine resin, aminomethyl resin, 4-benzyloxybenzyl alcohol resin, 4-methylbenzhydrylamine resin, PAM resin, 4-hydroxymethylphenyl acetamidomethyl resin, polyacrylamide resin, 4-(2',4'-dimethoxyphenyl-hydroxymethyl)phenoxy resin, 4-(2',4'-dimethoxyphenyl-Fmoc-aminoethyl)phenoxy resin, etc. Using such resins, amino acids in which α-amino groups and functional groups on the side chains are appropriately protected are condensed on the resin in the order of the sequence of the desired low molecular peptide according to various condensation methods known per se. At the end of the reaction, the low molecular peptide is excised from the resin and at the same time, the protecting groups are removed. Then, intramolecular disulfide bond-forming reaction is performed in a highly diluted solution to obtain the desired low molecular peptide or an amide form thereof.

For condensation of the protected amino acids described above, a variety of activation reagents for peptide synthesis can be used, but carbodiimides are particularly preferably employed. Examples of such carbodiimides include DCC, N,N'-diisopropylcarbodiimide, and N-ethyl-N'-(3-dimethylaminopropyl)carbodiimide. For activation by these reagents, the protected amino acids in combination with a racemization inhibiting additive (e.g., HOBt, HOOBt) are added directly to the resin, or the protected amino acids are previously activated in the form of symmetric acid anhydrides, HOBt esters or HOOBt esters, followed by adding the thus activated protected amino acids to the resin.

Solvents suitable for use in the activation of the protected amino acids or the condensation with the resin may be appropriately selected from solvents that are known to be usable for peptide condensation reactions. Examples of such solvents include acid amides such as N,N-dimethylformamide, N,N-dimethylacetamide and N-methylpyrrolidone; halogenated hydrocarbons such as methylene chloride and chloroform; alcohols such as trifluoroethanol; sulfoxides such as dimethylsufoxide; ethers such as pyridine, dioxane and tetrahydrofuran; nitrites such as acetonitrile and propionitrile; esters such as methyl acetate and ethyl acetate; and appropriate mixtures of these solvents.

The reaction temperature is appropriately selected from the range known to be applicable to peptide bond-forming reactions and is generally selected in the range of about −20° C. to about 50° C. The activated amino acid derivatives are used generally in an excess amount of 1.5 to 4 times. As a result of a test using the ninhydrin reaction, it was found that when the condensation is insufficient, the condensation can be completed by repeating the condensation reaction without removing of the protecting groups. When the condensation is yet insufficient even after repeating the reaction, unreacted amino acids are acetylated with acetic anhydride or acetylimidazole.

Examples of protecting groups used to protect the amino group of the starting material include Z, Boc, tert-pentyloxycarbonyl, isobornyloxycarbonyl, 4-methoxybenzyloxycarbonyl, Cl-Z, Br-Z, adamantyloxycarbonyl, trifluoroacetyl, phthaloyl, formyl, 2-nitrophenylsulphenyl, diphenylphosphinothioyl, Fmoc, etc.

The carboxyl group can be protected by, e.g., alkyl esterification (e.g., esterification of linear, branched or cyclic alkyl such as methyl, ethyl, propyl, butyl, tert-butyl, cyclopentyl, cyclohexyl, cycloheptyl, cyclooctyl, 2-adamantyl), aralkyl esterification (e.g., benzyl esterification, 4-nitrobenzyl esterification, 4-methoxybenzyl esterification, 4-chlorobenzyl esterification, benzhydryl esterification), phenacyl esterification, benzyloxycarbonyl hydrazidation, tert-butoxycarbonyl hydrazidation, trityl hydrazidation, etc.

The hydroxyl group of serine can be protected by, for example, esterification or etherification. Examples of groups suitably used for the esterification include a lower alkanoyl group such as an acetyl group, an aroyl group such as a benzoyl group, a group derived from carbonic acid such as a benzyloxycarbonyl group and an ethoxycarbonyl group, etc. Examples of a group suitably used for the etherification include a benzyl group, a tetrahydropyranyl group, a tert-butyl group, etc.

Examples of protecting groups for the phenolic hydroxyl group of tyrosine include Bzl, $Cl_2$-Bzl, 2-nitrobenzyl, Br-Z, tert-butyl, etc.

Examples of protecting groups for the imidazole moiety of histidine include Tos, 4-methoxy-2,3,6-trimethylbenzenesulfonyl, DNP, benzyloxymethyl, Bum, Boc, Trt, Fmoc, etc.

Examples of the activated carboxyl groups in the starting amino acids include the corresponding acid anhydrides, azides, activated esters (esters with alcohols (e.g., pentachlorophenol, 2,4,5-trichlorophenol, 2,4-dinitrophenol, cyanomethyl alcohol, p-nitrophenol, HONB, N-hydroxysuccimide, HOBt)), etc. Examples of the activated amino groups in the starting amino acids include the corresponding phosphoric amides.

Methods of eliminating (detaching) the protecting groups include acid treatment with anhydrous hydrogen fluoride, methanesulfonic acid, trifluoromethanesulfonic acid or trifluoroacetic acid, or a mixture solution of these acids; base treatment with diisopropylethylamine, triethylamine, piperidine, or piperazine; and reduction with sodium in liquid ammonia. The elimination reaction by the acid treatment described above is generally carried out at a temperature of about −20° C. to about 40° C. In the acid treatment, it is efficient to add a cation scavenger such as anisole, phenol, thioanisole, m-cresol, p-cresol, dimethylsulfide, 1,4-butanedithiol or 1,2-ethanedithiol. Furthermore, a 2,4-dinitrophenyl group known as a protecting group for the imidazole of histidine is removed by treatment with thiophenol. A formyl group used as a protecting group for the indole of tryptophan is eliminated by the above-mentioned acid treatment in the presence of 1,2-ethanedithiol or 1,4-butanedithiol, as well as by treatment with an alkali such as a dilute sodium hydroxide solution and dilute ammonia.

Protection of functional groups that should not be involved in the reaction of the starting material, the protecting groups, elimination of the protecting groups and activation of functional groups that are involved in the reaction, etc. may be appropriately selected from known groups and known means.

In another method for obtaining the object amidated low molecular peptide, for example, the α-carboxyl group of the carboxy terminal amino acid is first protected by amidation, and the peptide chain is then extended from the amino group side up to the desired length. Thereafter, a partial peptide in which only the protecting group of the N-terminal α-amino group of the peptide chain has been eliminated and a partial peptide in which only the protecting group of the C-terminal carboxyl group has been eliminated are produced. The two partial peptides are condensed in a solvent mixture described above. The details of the condensation reaction are the same as described above. After the protected peptide obtained by the condensation is purified, and all the protecting groups are then eliminated by the method described above to give the desired crude low molecular peptide. This crude low molecular peptide can be purified by various known purification means. Lyophilization of the major fraction gives the amide form of the desired low molecular peptide.

To prepare the esterified form of the low molecular peptide, for example, the α-carboxyl group of the carboxy terminal amino acid is condensed with the desired alcohol to prepare the amino acid ester, which is subjected to a procedure similar to the preparation of the amidated low molecular peptide described above to give the desired esterified low molecular peptide.

After the reaction, the product may be isolated and purified by a combination of conventional purification methods such as solvent extraction, distillation, column chromatography, liquid chromatography and recrystallization to give the objective peptide. When the low molecular peptide obtained by the above methods is in a free form, the peptide can be converted into a suitable salt by a known method. When the peptide is obtained in a salt form, it can be converted into a free form by a known method.

More specifically, the erythropoietin receptor antagonist or a salt thereof to be contained in the agent of the present invention is prepared by a method described in Biochemistry 37, 3699, 1998.

The erythropoietin receptor antagonist or a salt thereof to be contained in the agent of the present invention may be an anti-erythropoietin receptor antibody or a salt thereof.

The antibody against an erythropoietin receptor or a salt thereof may be either a polyclonal antibody or a monoclonal antibody as long as it can recognize an erythropoietin receptor or a salt thereof.

The antibody against an erythropoietin receptor or a salt thereof (hereinafter sometimes referred to as an erythropoietin receptor, etc.) can be prepared according to a known method for preparing an antibody or an antiserum using an erythropoietin receptor as the antigen.

[Preparation of Monoclonal Antibody]

(a) Preparation of Monoclonal Antibody Producer Cells

An erythropoietin receptor or the like is administered alone or in combination with a carrier or a diluent to a mammal at a site that can produce the antibody. In order to enhance the antibody productivity, Freund's complete adjuvant or Freund's incomplete adjuvant may be administered. The administration is effected usually once every 2 to 6 weeks and about 2 to 10 times in total. Mammals to be used include monkeys, rabbits, dogs, guinea pigs, mice, rats, sheeps, and goats. Preferably, mice and rats are used.

For preparing monoclonal antibody producer cells, an individual that shows an antibody titer is selected from warm-blooded animals, e.g., mice, immunized with the antigen, and then the spleen or lymph node is removed after 2 to 5 days of the final immunization. Monoclonal antibody producer hybridoma cells can be prepared by fusion of the antibody producer cells contained in the spleen or lymph node with myeloma cells. The antibody titer in the antiserum can be determined, for example, by reacting a labeled erythropoietin receptor as described below or the like with the antiserum and then measuring the activity of the labeling agent bound to the antibody. The fusion can be carried out according to any known method, for example, the method of Kohler and Milstein (Nature, 256, 495, 1975). Examples of a fusion accelerator are polyethylene glycol (PEG), Sendai virus, etc. Preferably, PEG is used.

Examples of myeloma cells include NS-1, P3U1, SP2/0, etc. Preferably, P3U1 is used. The ratio of the number of the antibody producer cells (spleen cells) to the number of myeloma cells to be used is preferably about 1:1 to about 20:1. The cell fusion may be carried out efficiently by adding PEG (preferably PEG 1000 to PEG 6000) at a concentration of about 10% to about 80%, followed by incubation at about 20° C. to about 40° C., preferably about 30° C. to about 37° C. for about 1 minute to about 10 minutes.

For screening monoclonal antibody producer hybridomas, various methods can be used. Examples of such methods include a method which comprises adding a culture supernatant of hybridoma to a solid phase (e.g., microplate) on which an antigen such as an erythropoietin receptor is adsorbed directly or together with a carrier, adding an anti-immunoglobulin antibody (where mouse cells are used for the cell fusion, anti-mouse immunoglobulin antibody is used) labeled with a radioactive substance, an enzyme or the like, or Protein A, and then detecting a monoclonal antibody bound to the solid phase; and a method which comprises adding a culture supernatant of hybridoma to a solid phase on which an anti-immunoglobulin antibody or Protein A is adsorbed, adding an erythropoietin receptor or the like labeled with a radioactive substance or an enzyme and then detecting a monoclonal antibody bound to the solid phase.

Monoclonal antibodies can be selected according to known methods or similar methods thereto. In general, the selection can be effected in a medium for animal cells supplemented with HAT (hypoxanthine, aminopterin and thymidine). Any media in which hybridoma cells can grow may be used for screening and growing. For example, RPMI 1640 medium containing 1% to 20%, preferably 10% to 20% fetal bovine serum, GIT medium containing 1% to 10% fetal bovine serum (Wako Pure Chemical Industries, Ltd.), a serum free medium for culturing hybridomas (SFM-101, Nissui Pharmaceutical Co., Ltd.), etc. can be used. The culture temperature is usually 20° C. to 40° C., preferably about 37° C. The culture period is usually about 5 days to about 3 weeks, preferably 1 to 2 weeks. The culture may be usually carried out in 5% $CO_2$. The antibody titer of the culture supernatant of a hybridoma can be determined as in the determination of antibody titer in antisera described above.

(b) Purification of Monoclonal Antibody

Isolation and purification of a monoclonal antibody can be carried out according the same manner as applied to conventional isolation and purification of polyclonal antibodies, for example, a method of isolation and purification of immunoglobulins (for example, salting-out, alcohol precipitation, isoelectric point precipitation, electrophoresis, adsorption and desorption with ion exchangers (e.g., DEAE), ultracentrifugation, gel filtration, or a specific purification method in which an antigen-binding solid phase or an activated adsorbent such as Protein A or Protein G is used to collect only an antibody, and the binding is dissociated to obtain the antibody).

[Preparation of Polyclonal Antibody]

The polyclonal antibody of the present invention can be produced by known methods or similar methods thereto. For example, the polyclonal antibody can be produced by forming a complex between an immune antigen (an antigen such as a erythropoietin receptor, etc.) and a carrier protein, immunizing a mammal with the complex in a manner similar to the method described above for a monoclonal antibody, collecting the product containing an antibody against the erythropoietin receptor, etc. from the immunized animal, and then isolating and purifying the antibody.

As for the complex between an immune antigen and a carrier protein used for immunizing a mammal, the type of the carrier protein and the mixing ratio between the carrier and hapten may be any type and in any ratio as long as the antibody can be efficiently produced to the hapten, which is crosslinked with the carrier and used for immunization. For example, bovine serum albumin, bovine thyroglobulin or keyhole limpet hemocyanin is coupled to hapten in a carrier-to-hapten weight ratio of about 0.1 to about 20, preferably about 1 to about 5.

A variety of condensation agents can be used for the coupling of a carrier to hapten. Glutaraldehyde, carbodiimide, maleimide activated ester and activated ester reagents containing a thiol group or a dithiopyridyl group, etc. can be used for the coupling.

The condensation product is administered alone or together with a carrier or a diluent to a warm-blooded animal at a site capable of producing an antibody. In order to enhance the antibody productivity, Freund's complete adjuvant or Freund's incomplete adjuvant may be administered. The administration is usually carried out once every 2 to 6 weeks and 3 to 10 times in total.

The polyclonal antibody can be collected from the blood, ascites, etc., preferably from the blood of mammals immunized by the above-mentioned method.

The polyclonal antibody titer in the antiserum can be determined by the same procedure as in the serum antibody titer described above. The polyclonal antibody can be isolated and purified according to the same method for isolation and purification of an antibody as used for the monoclonal antibody described above.

Since the erythropoietin receptor antagonist or a salt thereof or a prodrug thereof to be contained in the agent of the present invention has an inhibitory effect on tumor proliferation, etc., the agent of the present invention is useful as a agent for prophylaxis or treatment of proliferative organ diseases (e.g., primary, metastatic or recurrent tumors such as breast cancer, prostate cancer, pancreatic cancer, gastric cancer, pulmonary cancer, bowel cancer (colon cancer, rectum cancer, anal cancer), esophageal cancer, duodenal cancer, head and neck cancer (lingual cancer, pharyngeal cancer, larynx cancer), brain tumor, neurilemmoma, non-small-cell pulmonary cancer, small-cell pulmonary cancer, hepatic cancer, renal cancer, bile duct cancer, uterus cancer (uterine body cancer, uterine cervical cancer), ovarian cancer, bladder cancer, skin cancer, angioma, malignant lymphoma, malignant melanoma, thyroid cancer, bone tumor, angioma, angiofibroma, retinal sarcoma, penile cancer, childhood solid cancer, Kaposi's sarcoma, Kaposi's sarcoma due to AIDS, maxillary sinus tumor, fibrous histiocytoma, smooth muscle sarcoma, rhabdomyosarcoma, liposarcoma, hysteromyoma, osteoblastoma, osteosarcoma, chondosarcoma, cancerous mesotherioma, leukemia, etc., etc.), chronic arthritic diseases such as rheumatoid arthritis, rheumatoid diseases, chronic arthritis of collagenosis, tendovaginitis, etc., interstitial proliferative disease such as hypertrophic scars, keloid, pulmonary fibrosis, etc. for mammals (e.g., mouse, rat, hamster, rabbit, cat, dog, bovine, sheep, monkey, human, etc.).

The agent of the present invention has low toxicity and is safe.

The erythropoietin receptor antagonist or a salt thereof or a prodrug thereof to be contained in the agent of the present invention has low toxicity, and can be safely administered alone or as a mixture with a pharmaceutically acceptable carrier in the form of a pharmaceutical preparation such as tablets (inclusive of sugar-coated tablets and film-coated tablets), powder, granules, capsules (inclusive of soft capsules), liquid agents, injection, suppositories or sustained-release agents according to a means known per se generally used for producing a pharmaceutical preparation, orally or parenterally (e.g., topically, rectally, intravenously, subcutaneously, intramuscularly, intranasally, intravaginally, via oral mucosa, via pulmonary mucosa or via transocular administration, etc.).

Examples of a pharmaceutically acceptable carrier that may be used for preparation of the agent of the present invention include various organic or inorganic carriers that are conventionally used as a pharmaceutical material. For example, excipients, lubricants, binders and disintegrators can be used for solid preparations; and solvents, solubilizing agents, suspending agents, isotonic agents, buffer agents, soothing agents, etc., can be used for liquid preparations. If necessary, conventional additives such as preservatives, antioxidants, coloring agents, sweetening agents, adsorbing agents and wetting agents can be also used in an appropriate amount.

Examples of excipients include lactose, white sugar, D-mannitol, starch, corn starch, crystalline cellulose, light anhydrous silicic acid, etc.

Examples of lubricants include magnesium stearate, calcium stearate, talc, colloidal silica, etc.

Examples of binders include crystalline cellulose, white sugar, D-mannitol, dextrin, hydroxypropyl cellulose, hydroxypropylmethyl cellulose, polyvinyl pyrrolidone, starch, sucrose, gelatin, methyl cellulose, carboxymethyl cellulose sodium, etc.

Examples of disintegrators include starch, carboxymethylcellulose, carboxymethylcellulose calcium, carboxymethyl starch sodium, L-hydroxypropylcellulose, etc.

Examples of solvents include water for injection, alcohol, propyleneglycol, Macrogol, sesame oil, corn oil, olive oil, etc.

Examples of solubilizing agents include polyethylene glycol, propylene glycol, D-mannitol, benzyl benzoate, ethanol, trisaminomethane, cholesterol, triethanolamine, sodium carbonate, sodium citrate, etc.

Examples of suspending agents include surfactants such as stearyl triethanolamine, sodium lauryl sulfate, laurylaminopropionic acid, lecithin, benzalkonium chloride, benzethonium chloride, glycerin monostearate, etc.; and hydrophilic polymers such as polyvinylalcohol, polyvinyl pyrrolidone, carboxymethyl cellulose sodium, methyl cellulose, hydroxymethyl cellulose, hydroxyethyl cellulose, hydroxypropyl cellulose, etc.

Examples of isotonic agents include glucose, D-sorbitol, sodium chloride, glycerin, D-mannitol, etc.

Examples of buffer agents include phosphate buffer, acetate buffer, carbonate buffer, citrate buffer, etc.

Examples of soothing agents include benzyl alcohol, etc.

Examples of preservatives include p-hydroxybenzoic esters, chlorobutanol, benzyl alcohol, phenethyl alcohol, dehydroacetic acid, sorbic acid, etc.

Examples of antioxidants include sulfite, ascorbic acid, α-tocopherol, etc.

The prepared injection solution is generally filled in a suitable ample. When be administered, the above-described composition for injection can be dissolved in a conventional aqueous diluent to form a liquid agent. Examples of the aqueous diluent include a glucose aqueous solution, saline, Ringer's solution, nutrition supplemental agent liquid, etc.

Since the thus obtained pharmaceutical preparation is safe and low toxic, it can be administered to human or non-human mammals (e.g., rat, mouse, rabbit, sheep, goat, swine, bovine, horse, cat, dog, monkey, etc.).

When the injection contains phosphoric acid or a salt thereof, the concentration of sodium phosphate or potassium phosphate in the injection is about 0.1 mM to 500 mM, preferably about 1 mM to 100 mM.

Methods of producing a sterile preparation include, but not limited to, a method in which the whole production steps are carried out aseptically, a gamma-ray sterilization method, a sterilization method by addition of an antiseptic, etc.

In the agent of the present invention, the content of the erythropoietin receptor antagonist or a salt thereof or a prodrug thereof varies depending on the form of the agent, and is generally about 0.1 to about 100 wt %, preferably about 10 to about 99.9 wt %, more preferably about 20 to about 90 wt % of the total amount of the agent.

In the agent of the present invention, the content of components other than the erythropoietin receptor antagonist or a salt thereof or a prodrug thereof varies depending on the form of the agent, and is generally about 10 to about 99.9 wt %, preferably about 20 to about 90 wt % of the total amount of the agent.

The dosage of the agent of the present invention varies depending on the kind of the erythropoietin receptor antagonist or a salt thereof or a prodrug thereof, the route of the administration, the condition, the age of the patient, etc. For example, in the case wherein the agent is administered parenterally (e.g., intravenously injected, etc.) for treatment of proliferative organ disease, the daily dosage is about 0.005 to about 50 mg, preferably about 0.05 to about 10 mg, more preferably about 0.2 to about 4 mg per 1 kg body weight of the erythropoietin receptor antagonist and it may be administered in 1 to 3 divided doses.

The agent of the present invention may comprise or may be used in combination with suitable amounts of other pharmaceuticals besides the erythropoietin receptor antagonist or a salt thereof or a prodrug thereof.

Examples of such a concomitant drug include various anticancer agents that can be used in treatment of proliferative organ diseases. Specific examples thereof include pharmaceuticals having low immune inhibitory effect such as endocrine therapeutic agents (LH-RH agonists and antagonists, sex hormone antagonists, sex hormone synthesis inhibitors, etc.), pharmaceuticals targeting for cancer-selective gene products (EGF receptor, HER2/erb-2, HER3/erb-3, HER4/erb-4, PDGF receptor, VEGF receptor, etc.) such as tyrosine kinase, chemotherapeutic agents, and agents for cancer vaccine therapy, etc.

Examples of agents for cancer vaccine therapy include (1) proteins derived from tumor antigens or similar tumor cells and fragment peptides thereof, and fused proteins comprising said proteins or peptides, (2) DNA fragments encoding said proteins or peptides and being capable of expression in vivo, and liposomes comprising said fragments, and (3) viruses or plasmids comprising said DNA fragments.

Examples of proteins derived from tumor cells which can be used as an agent for cancer vaccine therapy include melanoma-related antigens (e.g., MAGE-1, MAGE-3, MART-1, gp100, tyrosine kinase, etc.), prostate specific antigens (PSA), HER2 protein, MUC-1 mucin, hCG, gastrin, heat shock protein, E7 protein of human papilloma virus, carcinoembryonic antigens (CEA), mutated Ras protein, etc.

Accordingly, the agent of the present invention exhibits superior prophylactic or therapic effect on proliferative organ diseases even if used alone. Alternatively, it can be used as a combination with one or two kinds of the agent. Furthermore, the effect can be increased by concomitantly using the agent with one or more of other anticancer agents (concomitant use of multiple drugs). Another advantage of the concomitant use is that the amount used of the each drug can be reduced, which decreases side effects and remarkably contributes to improvement in Quality of Life for cancer patients (e.g., alleviation of Performance Stasis and pain, suppression of edema, an increase in apetite, an increase in body weight, etc.).

Specific examples of the concomitant agent that can be used with the agent of the present invention are as follows.

Examples of the "endocrine therapeutic agents" include fosfestrol, diethylstilbestrol, chlorotrianisene, medroxyprogesterone acetate, megestrol acetate, chlormadinone acetate, cyproterone acetate, danazol, allylestrenol, gestrinone, mepartricin, raloxifene, ormeloxifene, levormeloxifene, antiesterogens (e.g., tamoxifen citrate, toremifene citrate, etc.), pill preparations, mepitiostane, testololactone, aminoglutethimide, LH-RH agonists (e.g., goserelin acetate, buserelin acetate, leuprorelin acetate, etc.), droloxifene, epitiostanol, ethinylestradiol sulfonate, aromatase inhibitors (e.g., fadrozole hydrochloride, anastrozole, letrozole, exemestane, vorozole, formestane, etc.), antiandrogens (e.g., flutamide, bicalutamide, nilutamide, etc.), 5α-reductase inhibitors (e.g., finasteride, episteride, etc.), adrenocorticoids (e.g., dexamethasone, prednisolone, betamethasone, triamcinolone, etc.), androgen synthesis inhibitors (e.g., abiraterone, etc.), retinoids and retinoid metabolism retardants (e.g., liarozole etc.), etc.

Examples of the "chemotherapeutic agent" include alkylating agents, antimetabolites, anticancer antibiotics, anticancer agents derived from plants, etc.

Examples of the "alkylating agents" include nitrogen mustard, nitrogen mustard N-oxide hydrochloride, chlorambucil, cyclophosphamide, ifosfamide, thiotepa, carboquone, improsulfan tosylate, busulfan, nimustine hydrochloride, mitobronitol, melphalan, dacarbazine, ranimustine, estramustine phosphate sodium, triethylenemelamine, carmustine, lomustine, streptozocin, pipobroman, etoglucid, carboplatin, cisplatin, miboplatin, nedaplatin, oxaliplatin, altretamine, ambamustine, dibrospidium hydrochloride, fotemustine, prednimustine, pumitepa, ribomustine, temozolomide, treosulfan, trofosfamide, zinostatin stimalamer, carboquone, adozelesin, cystemustine, bizelesin, etc.

Examples of the "antimetabolites" include mercaptopurine, 6-mercaptopurine riboside, thioinosine, methotrexate, enocitabin, cytarabine, cytarabine ocfosfate, ancitabine hydrochloride, 5-FU drugs (e.g., fluorouracil, tegafur, UFT, doxifluridine, carmofur, galocitabine, emitefur, etc.), aminopterin, calcium leucovorin, tabloid, butocin, calcium folinate, calcium levofolinate, cladribine, emitefur, fludarabine, gemcitabine, hydroxycarbamide, pentostatin, piritrexim, idoxuridine, mitoguazone, tiazofurin, ambamustine, etc.

Examples of the "anticancer antibiotics" include actinomycin D, actinomycin C, mitomycin C, chromomycin A3, bleomycin hydrochloride, bleomycin sulfate, peplomycin sulfate, daunorubicin hydrochloride, doxorubicin hydrochloride, aclarubicin hydrochloride, pirarubicin hydrochloride, epirubicin hydrochloride, neocarzinostatin, mithramycin, sarkomycin, carzinophilin, mitotane, zorbicin hydrochloride, mitoxantrone hydrochloride, idarubicin hydrochloride, etc.

Examples of the "anticancer agents derived from plants" include etoposide, etoposide phosphate, vinblastine sulfate, vincristine sulfate, vindesine sulfate, teniposide, paclitaxel, docetaxel, vinorelbine, etc.

Examples of the "immunotherapeutic agents (BRM)" include picibanil, krestin, schizophyllan, lentinan, ubenimex, interferons, interleukins, macrophage colony stimulating factor, granulocyte colony stimulating factor, lymphotoxin, BCG vaccine, *Corynebacterium parvum,* levamisole, polysaccharide K, procodazole, etc.

The "cell growth factor" in the "drug that inhibits the effect of cell growth factor and receptor thereof" may be any substance as long as it promotes proliferation of cells and generally includes peptides having a molecular weight of not more than 20,000 and capable of exerting the action at a low concentration through binding to a receptor. Specifically, there can be mentioned (1) EGF (epidermal growth factor) or substances having the substantially the same activity [e.g., EGF, heregulin (HER2 ligand), etc.], (2) insulin or substances having substantially the same activity [e.g., insulin, IGF (insulin-like growth factor)-1, IGF-2, etc.], (3) FGF (fibroblast growth factor) or substances having substantially the same activity (acidic FGF, basic FGF, KGF (keratinocyte growth factor), FGF-10, etc.), and (4) other cell growth factors [e.g., CSF (colony stimulating factor), IL-2 (interleukin-2), NGF (nerve growth factor), PDGF (platelet-derived growth factor), TGF-β (transforming growth factor β), HGF (hepatocyte growth factor), VEGF (vascular endothelial growth factor, etc.), etc.

The above-mentioned "cell growth factor receptor" may be any receptor as long as it can bind to the above-mentioned cell growth factor, and examples thereof include EGF receptor, heregulin receptor (HER2), insulin receptor-1, insulin receptor-2, IGF receptor, FGF receptor-1, FGF receptor-2, etc.

The "drug that inhibits the effect of cell growth factor" includes herceptin (HER2 receptor antibody), etc.

Besides the above-mentioned drugs, L-asparaginase, aceglatone, procarbazine hydrochloride, protoporphyrin-cobalt complex salt, hematoporphyrin mercury sodium, topoisomerase I inhibitors (e.g., irinotecan, topotecan, etc.), topoisomerase II inhibitors (e.g., sobuzoxane, etc.), lyase inhibitors, endothelin antagonists (e.g., ABT-627, etc.), differentiation inducers (e.g., retinoid, vitamin D, etc.), neovascularization inhibitors, α-blockers (e.g., tamuslosin hydrochloride, etc.), insulin resistance improving agents (e.g., pioglitazone, rosiglitazone (maleate), GI-262570, JTT-501, MCC-555, YM-440, KRP-297, CS-011, FK-614, compounds described in WO99/58510 (e.g., (E)-4-[4-(5-methyl-2-phenyl-4-oxazolylmethoxy)benzyloxyimino]-4-phenyl-butyric acid, etc.), etc.), angiotensin II antagonists (e.g., losartan, eprosartan, candesartan cilexetil, valsartan, telmisartan, irbesartan, tasosartan, olmesartan and active metabolites thereof (e.g., candesartan, etc.), etc.), cancer antigens, DNA, lectin, glucide, lipid, etc. can also be used.

Examples of the salts of the concomitant drugs include salts similar to the above-mentioned salts of the erythropoietin receptor antagonist.

For the concomitant use of the agent of the present invention and the concomitant drug, the administration timing of the agent of the present invention and the concomitant drug is not specifically limited. The agent of the present invention and the concomitant drug may be administered simultaneously or separately with a time lag to a subject to be administered. The dosage of the concomitant drug may be determined based on clinically used dosage, and can be appropriately selected depending on the subject to be administered, administration route, disease, combination, etc.

The dosage forms of the agent of the present invention and the concomitant drug are not specifically limited as long as the agent of the present invention and the concomitant drug are combined when they are administered. Examples of such dosage form include (1) administration of a single preparation obtained by formulating the agent of the present invention and a concomitant drug together; (2) simultaneous administration of two different preparations obtained by formulating the agent of the present invention and a concomitant drug separately via the same administration route; (3) separate administration with a time lag of two different preparations obtained by formulating the agent of the present invention and a concomitant drug separately via the same administration route; (4) simultaneous administration of two different preparations obtained by formulating the agent of the present invention and a concomitant drug separately via different administration routes; and 5) separate administration with a time lag of two different preparations obtained by formulating the agent of the present invention and a concomitant drug separately via different administration routes (e.g., administration of the agent of the present invention followed by administration of a concomitant drug, or administration in the reverse order). Hereinafter these dosage forms are collectively abbreviated to the concomitant agent of the present invention.

The concomitant agent of the present invention has low toxicity, and a pharmaceutical composition can be prepared by mixing the agent of the present invention and/or the above-mentioned concomitant drug with a pharmaceutically acceptable carrier according to a method known per se.

A pharmaceutically acceptable carrier that may be used for preparation of the concomitant agent of the present invention may be similar to those for the above-mentioned pharmaceutical composition of the present invention.

When the agent of the present invention and the concomitant drug are formulated simultaneously and used as a single preparation, the content of the erythropoietin receptor antagonist or a salt thereof or a prodrug thereof in the concomitant agent of the present invention varies depending on the form of the preparation, and is generally about 0.1 to about 100 wt %, preferably about 10 to about 99.9 wt %, more preferably about 20 to about 90 wt % of the total amount of the preparation.

The content of a concomitant drug in the concomitant agent of the present invention also varies depending on the form of the preparation, and is generally about 0.1 to about 100 wt %, preferably about 10 to about 99.9 wt %, more preferably about 20 to about 90 wt % of the total amount of the preparation.

In the concomitant agent of the present invention, the content of components other than the erythropoietin receptor antagonist or a salt thereof or a prodrug thereof and the concomitant agent varies depending on the form of the preparation, and is generally about 10 to about 99.9 wt %, preferably about 20 to about 90 wt % of the total amount of the preparation.

The combination ratio between the erythropoietin receptor antagonist or a salt thereof or a prodrug thereof and a concomitant drug in the concomitant agent of the present invention can be appropriately selected depending on a subject to be administrated, route of administration, diseases, etc.

The dosage of the concomitant agent of the present invention varies depending on the kind of the erythropoietin receptor antagonist or a salt thereof or a prodrug thereof, the kind of the concomitant drug, route of administration, condition, age of a patient, etc. For example, in the case of oral administration for treatment of cancer, the daily dosage is about 0.005 to about 50 mg, preferably about 0.05 to about 10 mg, more preferably about 0.2 to about 4 mg per 1 kg body weight of the erythropoietin receptor antagonist or a salt thereof or a prodrug thereof and the concomitant drug and it may be administered in 1 to 3 divided doses.

The same contents may be applied to the case where the erythropoietin receptor antagonist to be contained in the agent of the present invention and a concomitant drug are formulated into different preparation respectively.

When the erythropoietin receptor antagonist to be contained in the agent of the present invention and a concomitant drug are formulated respectively into different preparations and subjected to concomitant use, the agent of the present invention and the pharmaceutical composition comprising a concomitant drug may be administered simultaneously. Alternatively, the agent of the present invention may be administered after the pharmaceutical composition comprising a concomitant drug is administered, or the pharmaceutical composition comprising a concomitant drug may be administered after the agent of the present invention is administered. When they are separately administered with a time lag, the time lag varies depending on the active component to be administered, dosage form, and administration method. For example, when the pharmaceutical composition comprising a concomitant drug is administered first, the agent of the present invention is administered within 1 min to 3 days, preferably 10 min to 1 day, more preferably 15 min to 1 hr after the pharmaceutical composition comprising a concomitant drug is administered. When the agent of the present invention is administered first, the pharmaceutical composition comprising a concomitant drug is administered within 1 min to 1 day, preferably 10 min to 6 hrs, more preferably 15 min to 1 hr after the agent of the present invention is administered.

The agent of the present invention can prevent or treat diseases more effectively by a combination of the administration alone or the concomitant administration with a concomitant drug as described above, and 1 to 3 kinds of non-drug therapies. Examples of non-drug therapy include operation, radiotherapy, gene therapy, thermotherapy, cryotherapy, burning therapy using laser, etc., and two or more kinds of these therapies can be combined.

For example, the agent of the present invention or the above-mentioned concomitant agent is used before or after an operation, or is used before or after treatment with a combination of two or three kinds of these therapies, whereby effects such as inhibition of expression of resistance, extension of Disease-Free Survival, suppression of metastasis or recurrence of cancer, life lengthening, etc. can be obtained.

The treatment using the agent of the present invention or the above-mentioned concomitant agent may also be combined with supportive therapy [(i) administration of antibiotics (e.g., β-lactams such as pansporin, macrolides such as clarithromycin) against various infectious complications, (ii) administration of high calorie parenteral fluid, an amino acid preparation or a multiple-vitamin preparation for improving malnutrition, (iii) administration of morphine for alleviating pain, (iv) administration of an agent for alleviating side effects such as nausea, vomit, loss of apetite, diarrhea, leukopenia, thrombocytopenia, decrease in hemoglobin concentration, alopecia, hepatopathy, nephropathy, DIC, and fever and (v) administration of an agent for suppressing multiple drug resistance of cancer, etc.].

Before or after the above-mentioned treatment, the agent of the present invention or the above-mentioned concomitant agent is preferably administered by oral administration (including sustained-release), intravenous administration (including bolus, infusion, clathrates), subcutaneous or intramuscular injection (inclusive of bolus, infusion, sustained-release), percutaneous, intratumor or proximal administration.

When the agent of the present invention or the above-mentioned concomitant agent is administered before an operation etc., it may be administered once about 30 min to about 24 hr before the operation etc., or may be administered in one to three cycles from about 3 months to about 6 months before an operation etc. Such administration of the agent of the present invention or the above-mentioned concomitant agent before an operation etc. can lead, for example, reduction in the size of cancer tissues, whereby the operation etc. can be carried out easily.

When the pharmaceutical composition of the present invention or the concomitant agent of the present invention is administered after an operation etc., it can be administered about 30 min to 24 hr after the operation etc., for example, repeatedly in the unit of several weeks to 3 months. Such administration of the agent of the present invention or the above-mentioned concomitant agent after an operation etc. can enhance the effect of the operation etc.

In the present specification and drawings, the codes of bases and amino acids are denoted in accordance with the IUPAC-IUB Commission on Biochemical Nomenclature or by the conventional codes in the art, examples of which are shown below. For amino acids that may have the optical isomers, L form is presented unless otherwise indicated.

DNA: deoxyribonucleic acid
cDNA: complementary deoxyribonucleic acid
Gly: glycine
Ala: alanine
Leu: leucine
Val: valine
Pro: proline
Ser: serine
Cys: cysteine
Thr: threonine
Tyr: tyrosine
His: histidine
Trp: tryptophan
Gln: glutamine
Lys: lysine
Phe: phenylalanine The sequence identification numbers (SEQ ID NO:) in the sequence listing of the present specification indicate the following sequence, respectively.

[SEQ ID NO: 1] Indicates the Amino Acid Sequence of EMP9.

The present invention is described in detail below with reference to Examples, Reference Examples and Test Examples. However, the scope of the present invention should not be construed to be limited to these.

EXAMPLE 1

1. Preparation of EMP9

EMP9 was synthesized by a known method and dissolved in saline. The solution was colored with addition of Evans blue at the final concentration of 0.25%.

2. Heterotransplantation

Five-week old nude mice (Balb/c Jcl-nu, Japan Clea Inc.) were purchased, maintained in a germfree chamber for a week for acclimatization and then used. $5 \times 10^6$ cells of malignant melanoma cell strains (P39, Utsumi and Elkind, 1993) were suspended in a culture solution (0.1 ml) and the suspension was injected subcutaneously interscapularly into the mice. After a few weeks, formation of tumor was observed on the outer skin surface. The major axis×minor axis×height of the tumor was measured twice a week. The tumor was observed until its size became 6×7×7 mm, thereafter administration was started. After the administration, the size of the tumor was measured in a similar manner.

3. Method of Administration

Four doses of 0.1 ml of a 0.5 mg/ml EMP9 solution were administered intraperitoneally at intervals of 1 hr. After 24 hr and 48 hr, 0.1 ml of the solution was administered similarly 4 times, respectively. On the 7th day from the first administration, the tumor was excised.

4. Analysis of Change in Tumor Due to Administration

The excised tumor was fixed in Zamboni fixing liquid or frozen in liquid nitrogen. The tumor fixed in Zamboni fixing liquid was divided into several tissue masses. The plural samples collected from the respective masses were embedded to prepare tissue sections thereof. The proliferating cells were stained using PCNA antibody and the vascular endothelial cells were stained using CD31 antibody, respectively. Hematoxylin was used for nuclear staining. Each of the section specimens was observed under a microscope at 200-fold magnification. The cell number in 20 compartments wherein one compartment has an area of $17.6 \times 10^{-3}$ mm$^2$ was counted (the cell number was not less than 4,500). The cell proliferation ratio was calculated from the following equation and represented in [Table 1]. Furthermore, the number of blood vessel in 100 compartments was counted, and the average number per a compartment ($13.1 \times 10^{-2}$ mm$^2$) was calculated and represented in [Table 1]. Static processing were carried out by Chi-square test for the cell proliferation ratio and by Student's t-test for the number of blood vessel, and a significant difference was observed between the group in which saline was administered and the group in which EMP9 was administered ($p<0.05$).

Proliferation ratio (%)=(number of proliferating cells/number of living cells)×100

TABLE 1

| Treatment | Proliferation ratio (%) | Number of blood vessel (average ± standard error) |
| --- | --- | --- |
| EMP9 | 3.03 | 0.64 ± 0.10 |
| Saline | 11.23 | 10.65 ± 0.56 |

The result of Table 1 shows that the EMP9 has superior inhibitory effects on both tumor proliferation and neovascular proliferation.

EXAMPLE 2

(1) EMP9: 10.0 g
(2) lactose: 60.0 g
(3) corn starch: 35.0 g
(4) gelatin: 3.0 g
(5) magnesium stearate: 2.0 g A mixture of EMP9 (10.0 g), lactose (60.0 g) and corn starch (35.0 g) was granulated by using 10 wt % aqueous gelatin solution (30 ml, 3.0 g as gelatin) and passing a sieve having a mesh size of 1 mm, and thereafter, the granules were dried at 40° C. and sieved again. The obtained granules were mixed with magnesium stearate (2.0 g) and the mixture was compressed. The obtained core tablets were coated with sugar coating consisting of an aqueous suspension of sucrose, titanium dioxide, talc and gum arabic. The coated tablets were glazed with beeswax to give coated tablets (1000 tablets).

EXAMPLE 3

(1) EMP9: 10.0 g
(2) lactose: 70.0 g
(3) corn starch: 50.0 g
(4) soluble starch: 7.0 g
(5) magnesium stearate: 3.0 g EMP9 (10.0 g) and magnesium stearate (3.0 g) were granulated using an aqueous solution of a soluble starch (70 ml, 7.0 g as soluble starch). The granules were dried and mixed with lactose (70.0 g) and corn starch (50.0 g). The mixture was compressed to give tablets (1000 tablets).

Reference Example 1

(1) leuprorelin acetate: 10.0 mg
(2) lactose: 70.0 mg
(3) corn starch: 50.0 mg
(4) solubilized starch: 7.0 mg
(5) magnesium stearate: 3.0 mg Leuprorelin acetate (10.0 mg) and magnesium stearate (3.0 mg) are granulated using an aqueous solution of a solubilized starch (0.07 ml, 7.0 mg as solubilized starch), and then the granules are dried and mixed with lactose (70.0 mg) and cornstarch (50.0 mg). The mixture is compressed to give tablets.

Preparation Example 1

The preparation obtained in Example 1 or 2 and the preparation obtained in Reference Example 1 are combined.

INDUSTRIAL APPLICABILITY

An erythropoietin receptor antagonist or a prodrug thereof has superior inhibitory effects on both tumor proliferation and neovascular proliferation, and is useful as an agent for prophylaxis or treatment of proliferative organ diseases, chronic arthritic diseases, hypertrophic scars or keloid. Specifically, it is effective against solid tumors with vascular proliferation.

The invention claimed is:

1. A method for prophylaxis or treatment of proliferative organ diseases, chronic arthritic diseases, hypertrophic scars or keloid, comprising administering an effective amount of an isolated erythropoietin receptor antagonist or a salt thereof to a mammal.

2. The method according to claim 1, wherein the isolated erythropoietin receptor antagonist or a salt thereof is an erythropoietin receptor antagonist having a molecular weight of 200 to 5000 or a salt thereof.

3. The method according to claim 1, wherein the isolated erythropoietin receptor antagonist or a salt thereof is a peptide consisting of 5 to 30 amino acid residues or a salt thereof.

4. The method according to claim 1, wherein the isolated erythropoietin receptor antagonist or a salt thereof is an erythropoietin mimetic peptide selected from the group consisting of EMP6, EMP7, EMP12, EMP22, EMP23, EMP24, EMP25, EMP33 and EMP39 or a salt thereof.

5. The method according to claim 1, wherein the isolated erythropoietin receptor antagonist or a salt thereof is EMP9 or a salt thereof.

6. The method according to claim 1, wherein the isolated erythropoietin receptor antagonist or a salt thereof is a peptide comprising an amino acid sequence having at least 70% homology to the amino acid sequence of SEQ ID NO: 1 or a salt thereof.

7. The method according to claim 1, wherein the isolated erythropoietin receptor antagonist or a salt thereof is an anti-erythropoietin receptor antibody or a salt thereof.

8. The method according to claim 1, wherein the proliferative organ disease is cancer or tumor.

9. The method according to claim 1, wherein the chronic arthritic disease is rheumatoid arthritis, rheumatoid diseases, chronic arthritis of collagenosis or tendovaginitis.

10. A method for suppressing vascular proliferation comprising administering an effective amount of an isolated erythropoietin receptor antagonist or a salt thereof to a mammal.

11. A method for prophylaxis or treatment of proliferative organ diseases, comprising administering an effective amount of an isolated erythropoietin receptor antagonist or a salt thereof in combination with an effective amount of another anticancer agent or a salt thereof to a mammal.

* * * * *